United States Patent [19]

Jullien

[11] Patent Number: 5,002,533
[45] Date of Patent: Mar. 26, 1991

[54] SYRINGE GUARD APPARATUS

[76] Inventor: Robert G. Jullien, 2904 Graham Rd., Falls Church, Va. 22042

[21] Appl. No.: 402,894

[22] Filed: Sep. 5, 1989

[51] Int. Cl.$^5$ ............................................. A61M 5/00
[52] U.S. Cl. .................................. 604/110; 604/192; 604/198; 604/263
[58] Field of Search ............... 604/110, 187, 192, 198, 604/263

[56] References Cited

U.S. PATENT DOCUMENTS 4,425,120  1/1984  Sampson et al. .................... 604/198
4,795,432  1/1989  Karczmer .......................... 604/110

Primary Examiner—John D. Yasko
Attorney, Agent, or Firm—Longacre & White

[57] ABSTRACT

A needle guard for use with a syringe barrel including a mechanism for selectively enabling and not enabling passage of a needle through the end of the guard. Further, the guard includes an end closure for permanently closing a needle aperture therein and positively destroying the needle upon telescopically moving the guard and syringe barrel to a respectively retracted position.

6 Claims, 19 Drawing Sheets

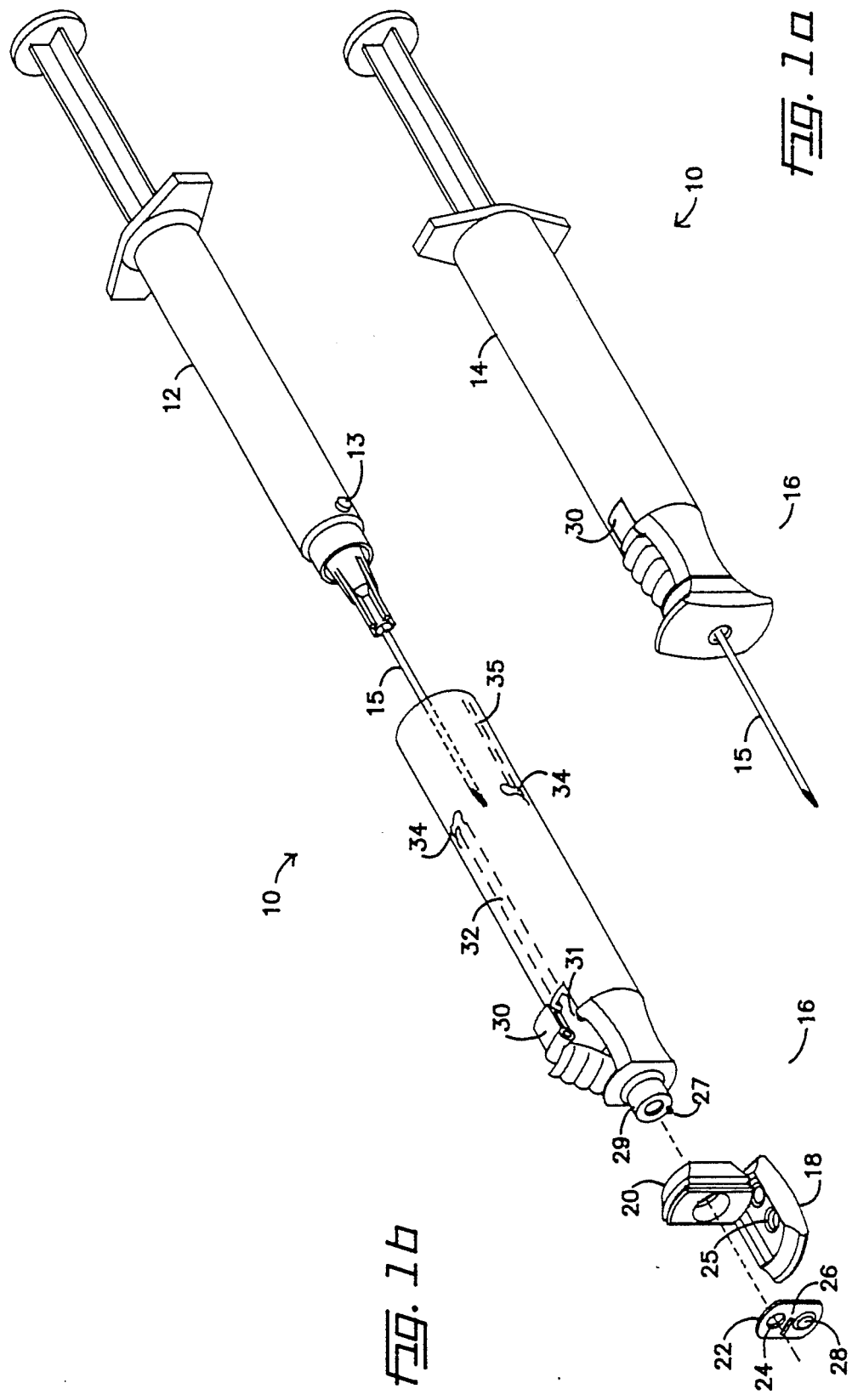

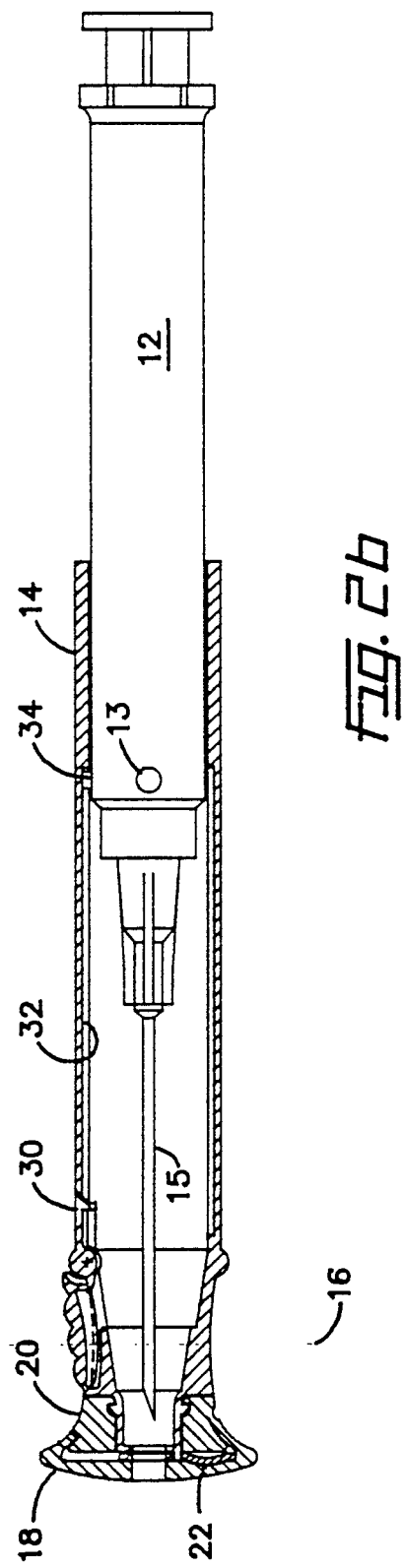
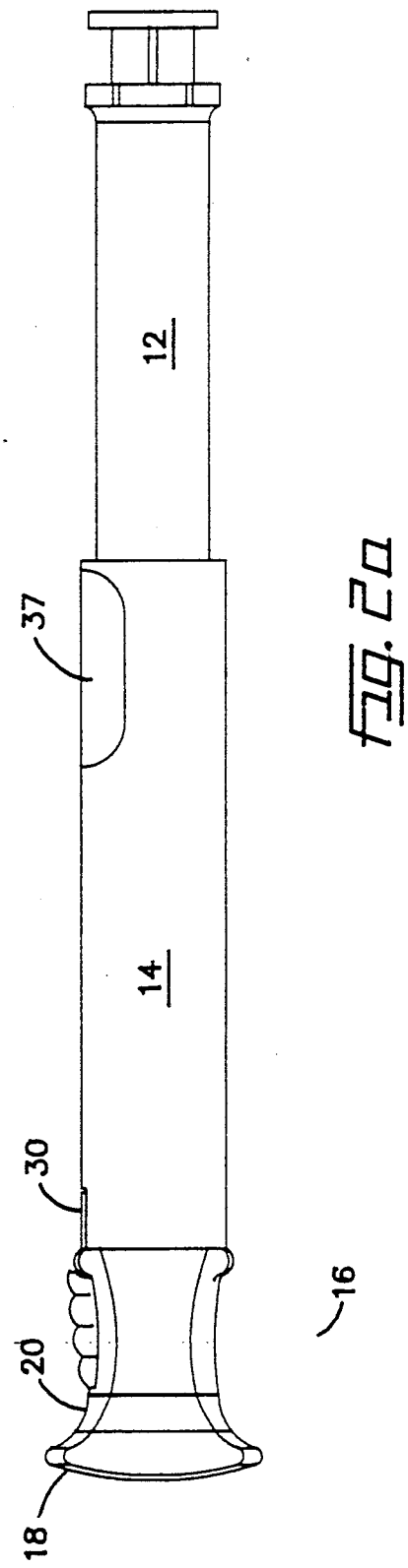

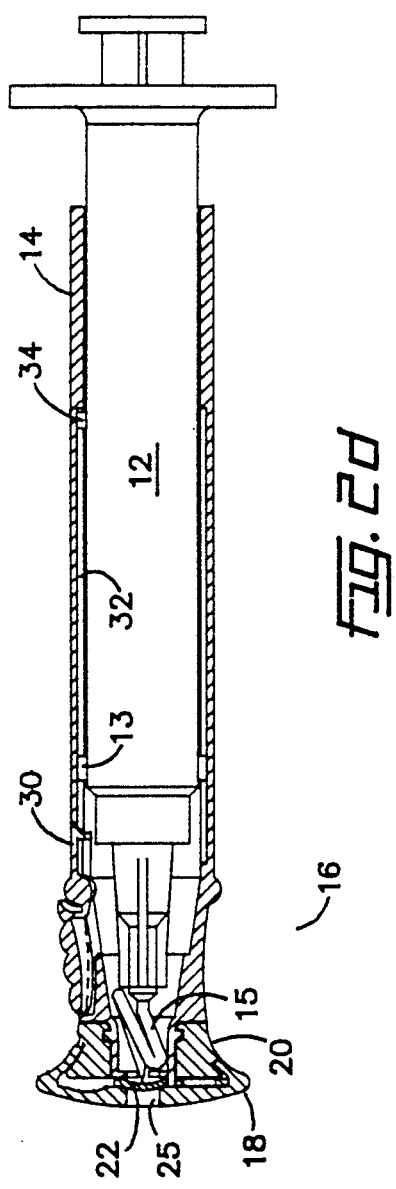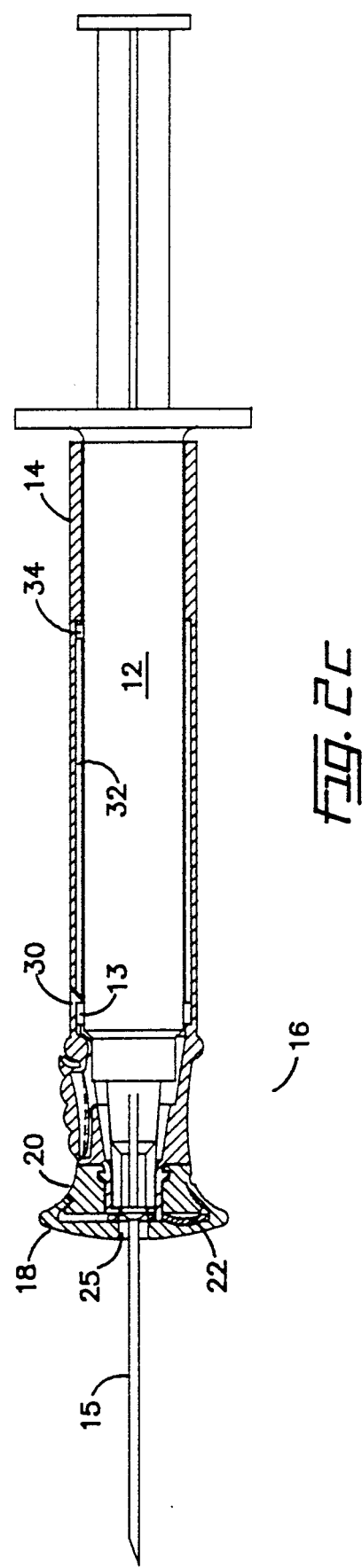

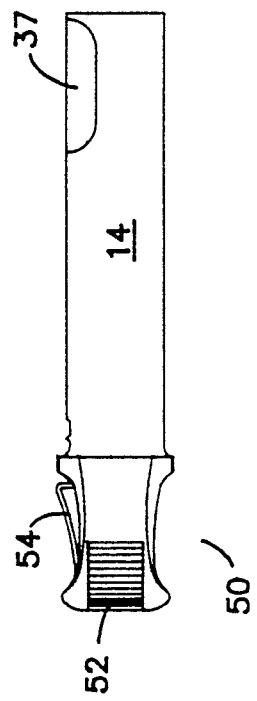
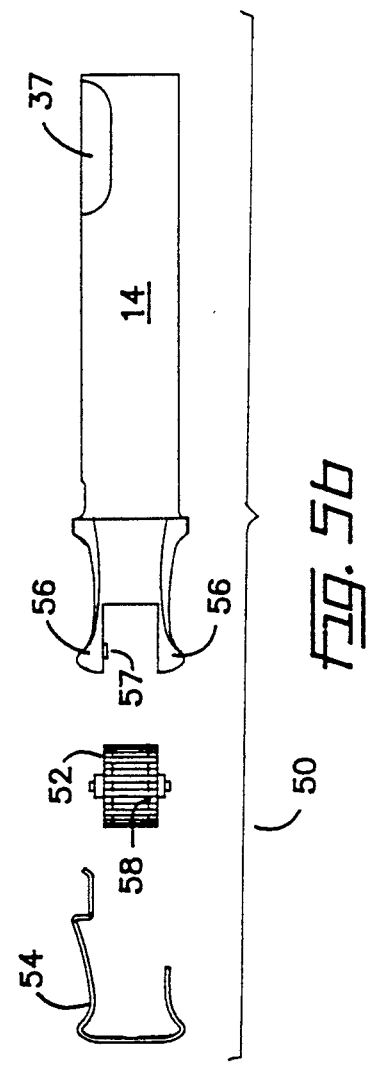
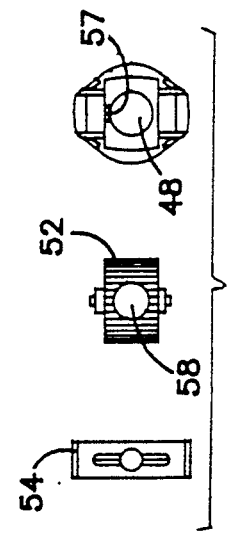
Fig. 5c
Fig. 5b
Fig. 5a

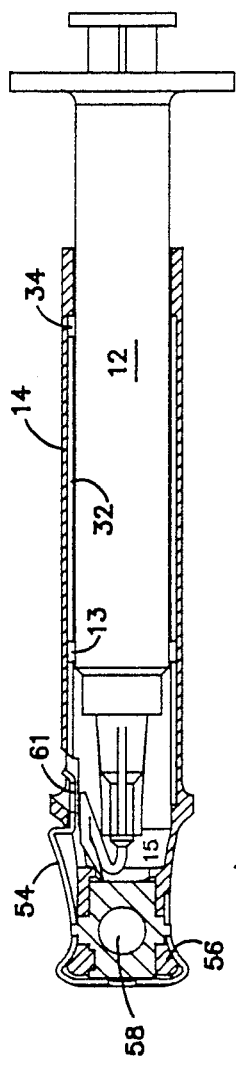
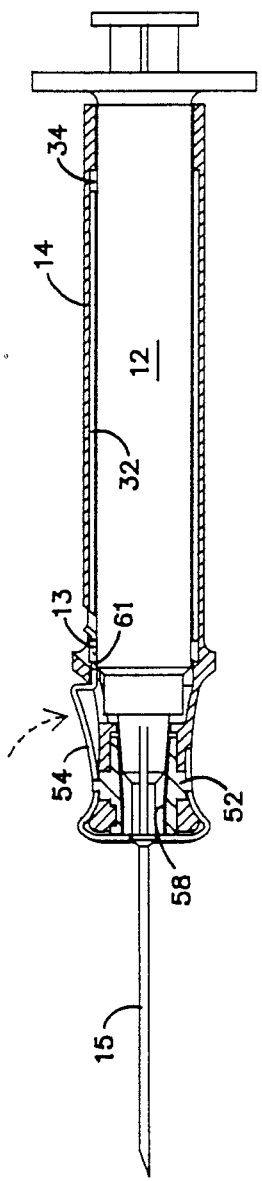
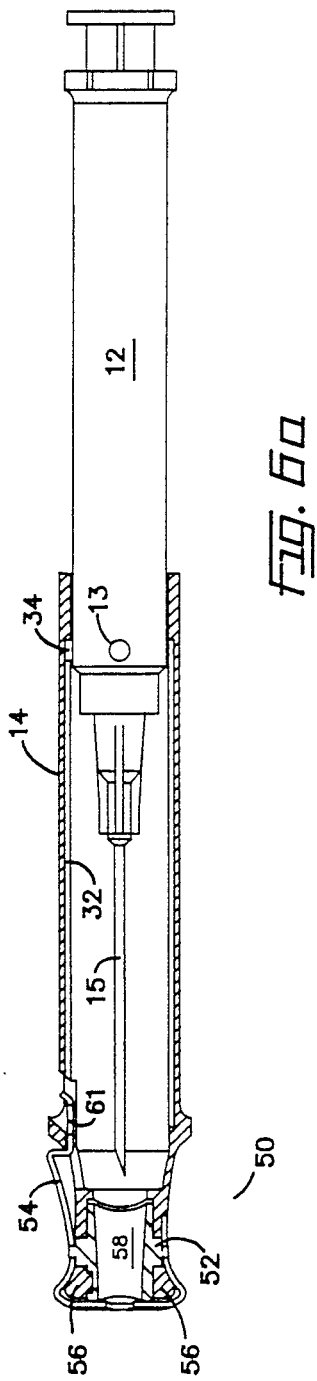

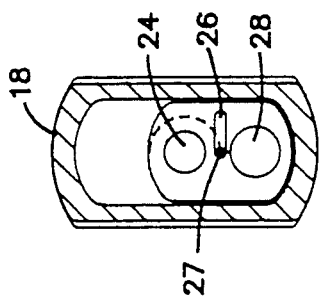
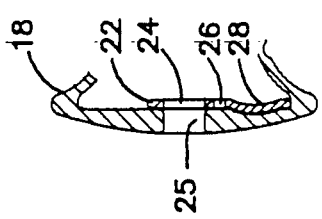
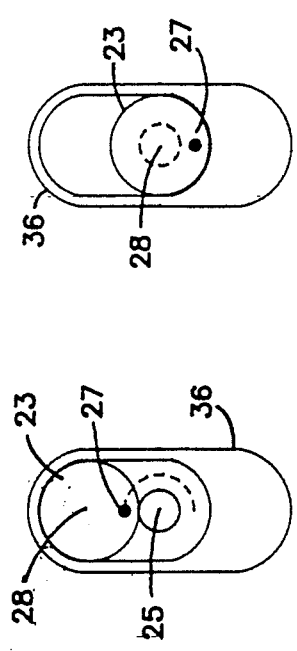
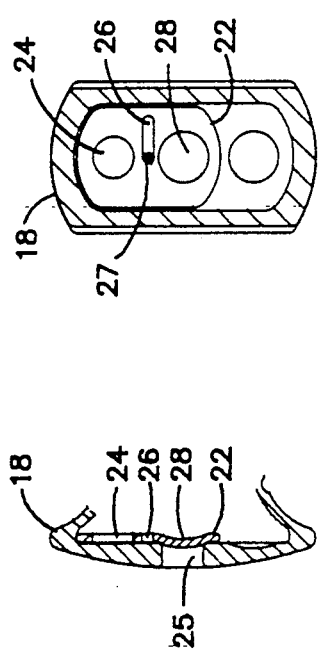

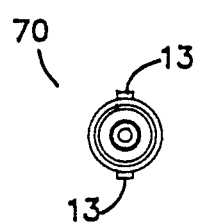 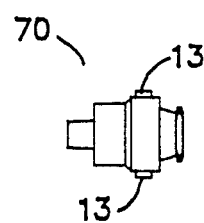 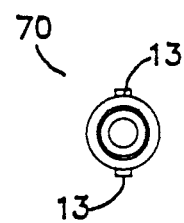
fig. 9a   fig. 9b   fig. 9c
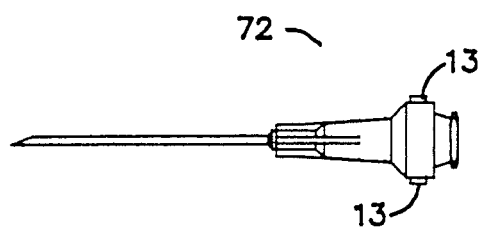 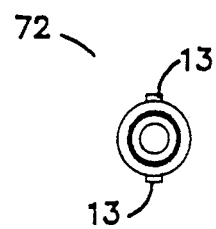
fig. 10a   fig. 10b
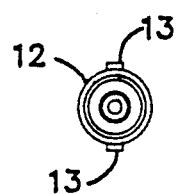 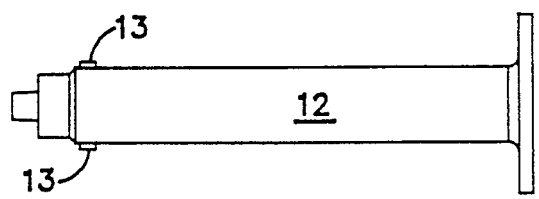
fig. 11a   fig. 11b

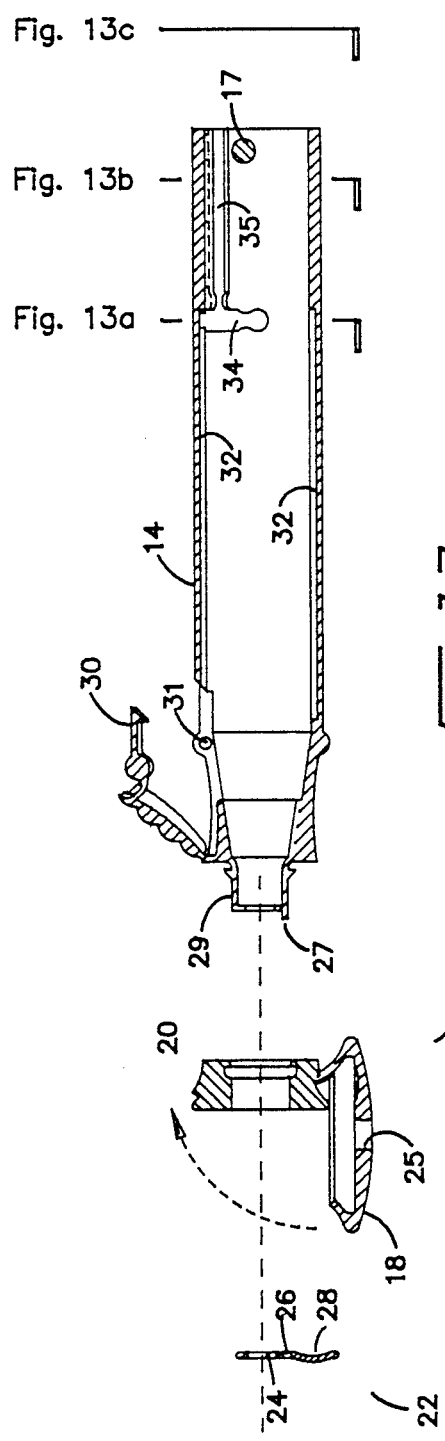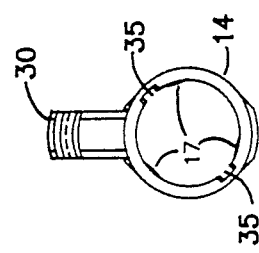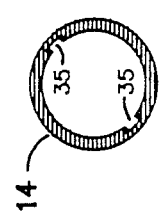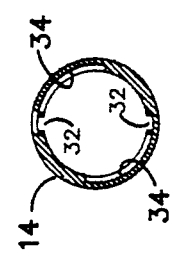

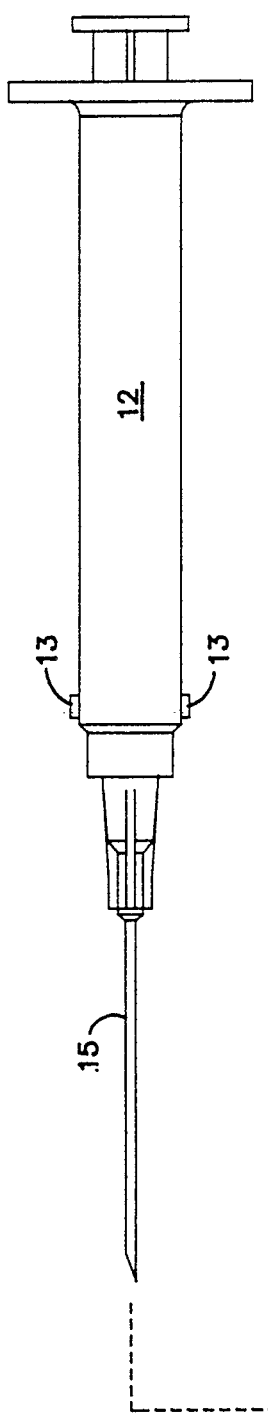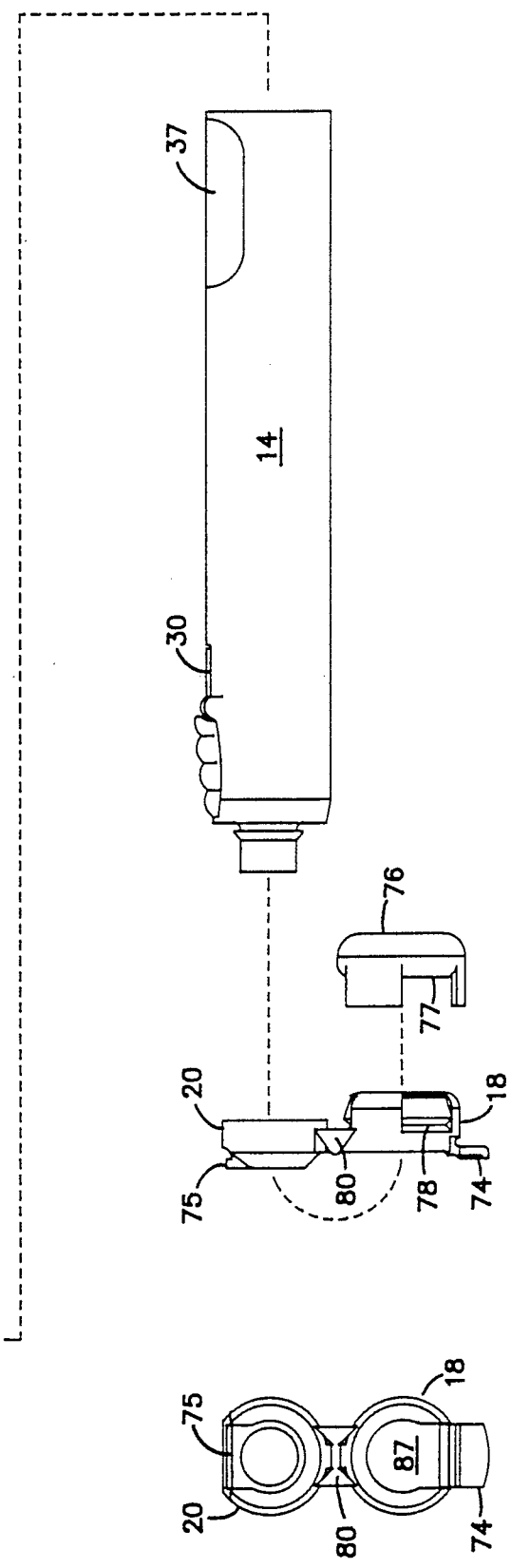
Fig. 14 a
Fig. 14 b

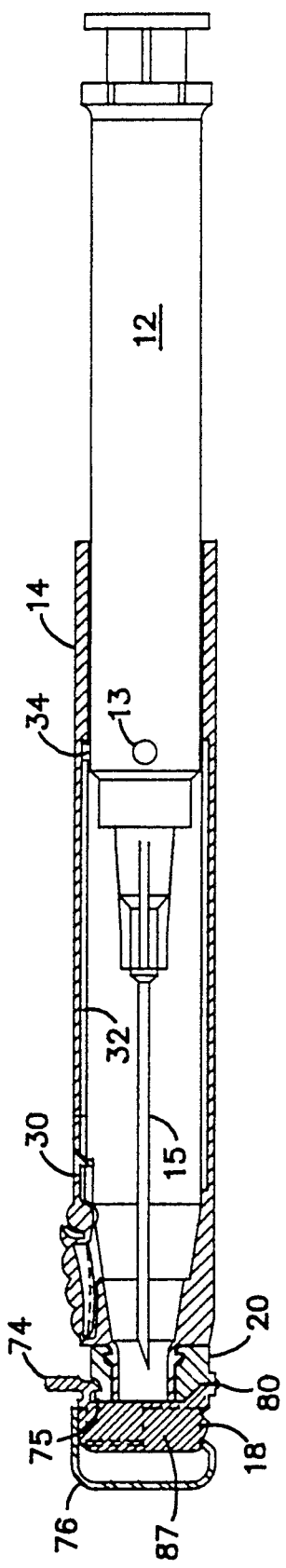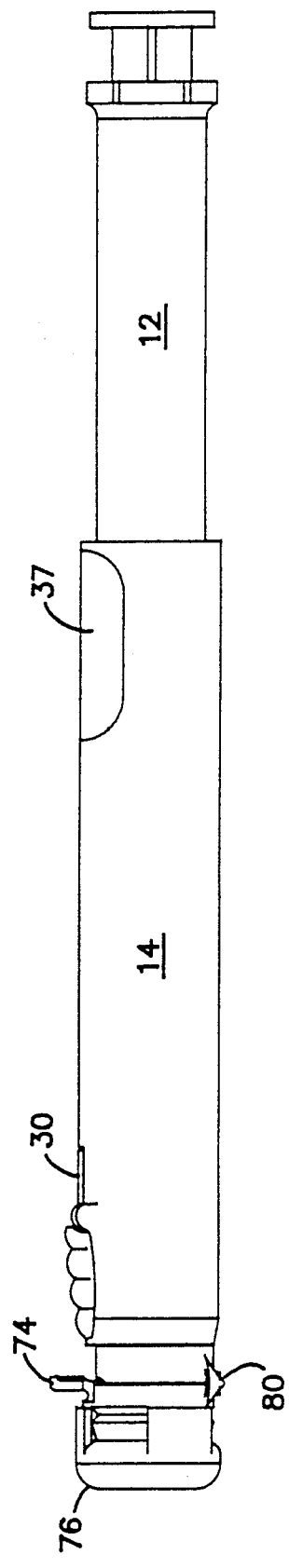

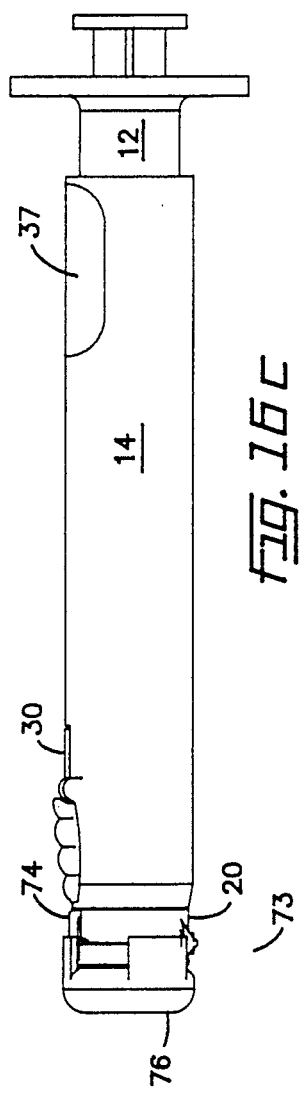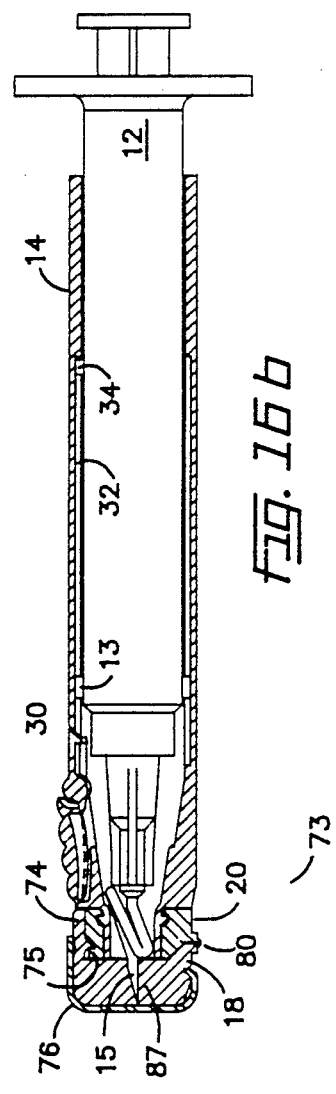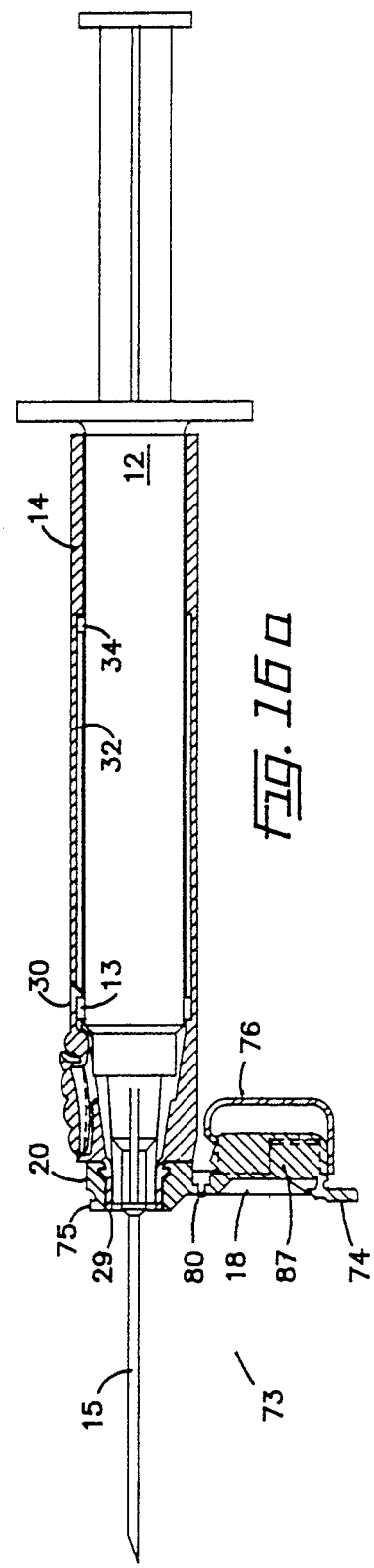

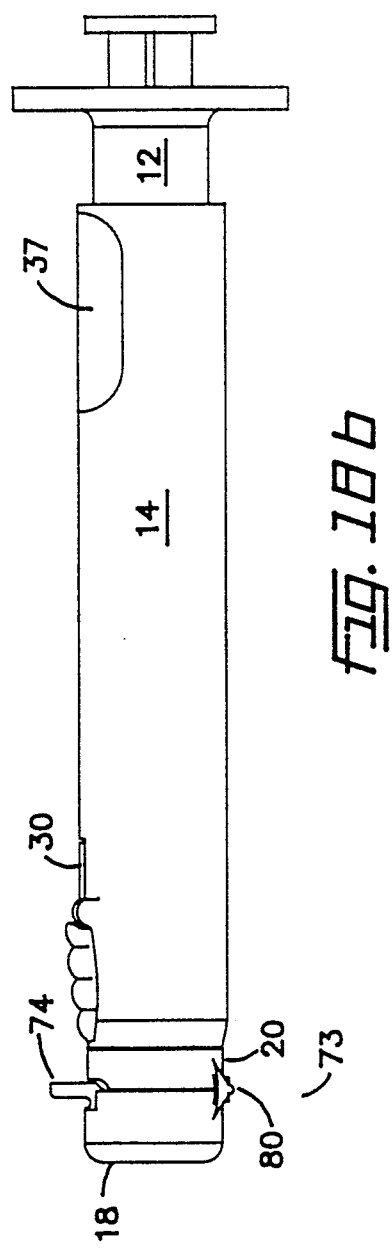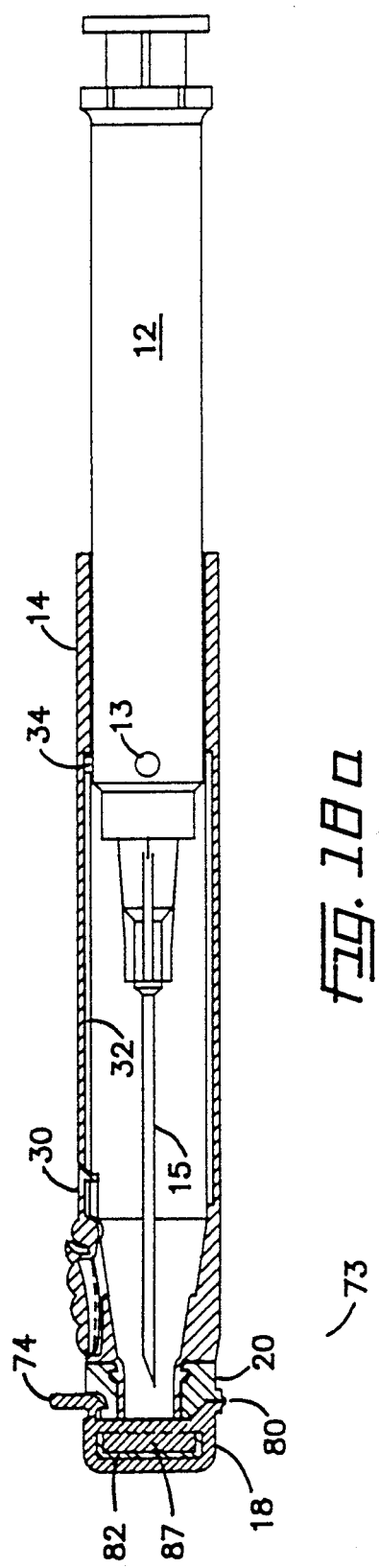
Fig. 18b
Fig. 18a

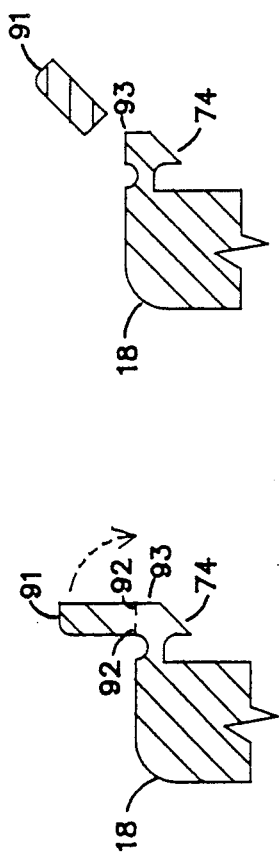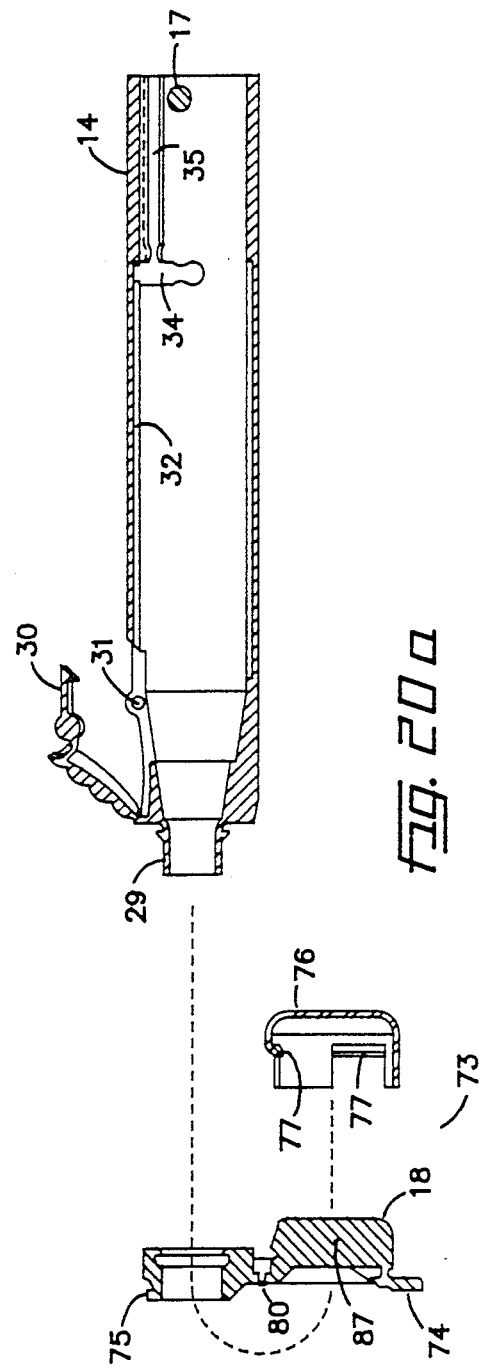

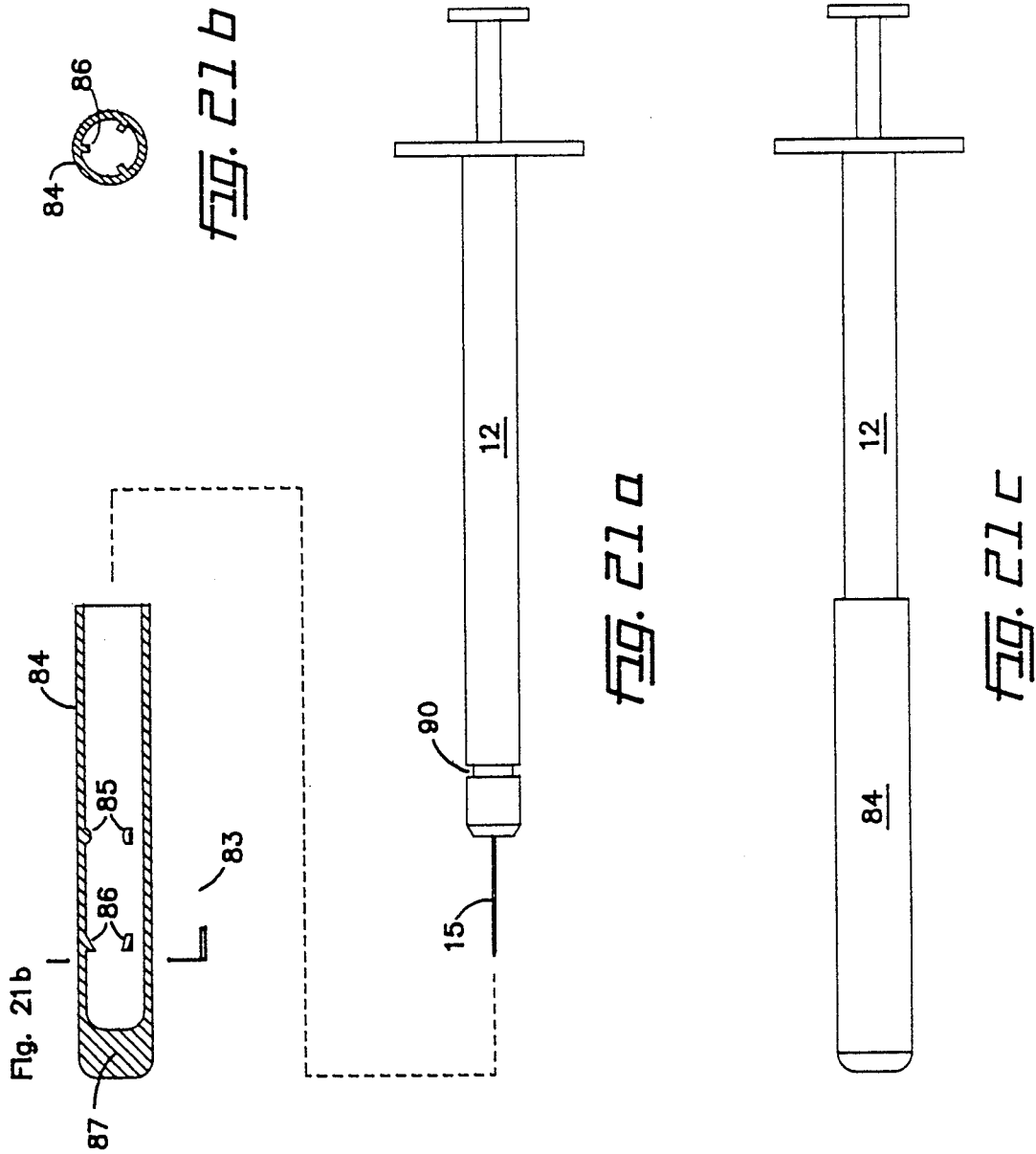

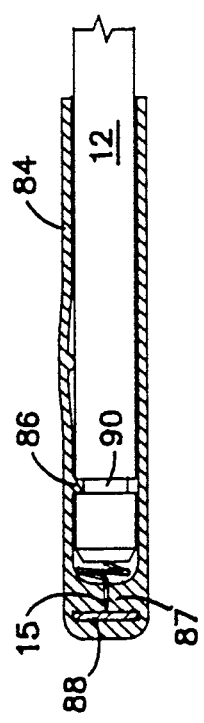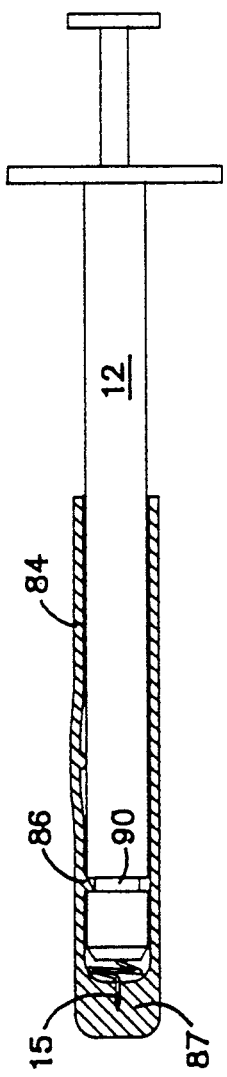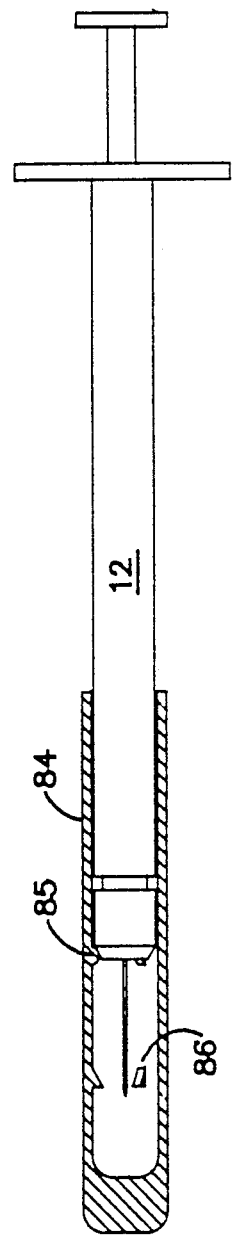

SYRINGE GUARD APPARATUS

PRIOR APPLICATION INFORMATION

This application is a continuation-in-part of application Ser. No. 07/360,585, filed June 2, 1989, entitled Syringe Guard Apparatus.

FIELD OF THE INVENTION

The present invention relates to the field of medical equipment. Specifically, the present invention relates to an apparatus for preventing unintended contact of a needle with foreign objects. Particularly, the prevention of needle-stick injuries which may occur when an injection is to be or has been given, or a sample been withdrawn, with respect to a patient, and the possible transmission of bloodborne or other fluidborne pathogens as a result of these injuries.

BACKGROUND OF THE INVENTION

Discoveries in medical science have long indicated that certain diseases are passed through unintended contact with contaminated needles. Specifically, blood to blood contact, or internal fluid to internal fluid contact, can spread diseases and pathogens which otherwise cannot be transmitted. To avoid such unintended transmission of pathogens by contaminated needles, particularly for medical professionals, several proposals have been advanced.

The most recent of these proposals has to do with widely available needle, syringe, and needle cap combinations. Specifically, certain governmental agencies are in the process of promulgating guidelines which outline several procedural methods of dealing with the inadvertent spread of infection through contaminated needles. While these procedural suggestions are useful, if they are unobserved, or a participant unavoidably fouls a needle against their person, the disease is none-the-less transmitted.

To address human fallibility with respect to following procedures, several needle guard type apparatus have been suggested. Specifically, guards which telescopically cover the syringe barrel and needle portion have been proposed. These guards may optionally include latching mechanisms at either end of the guard so as to hold the guard in a particular position with respect to the needle and syringe combination. Further, many of the guards are also proposed as permanent disposal devices for the needle so that if medical waste is improperly disposed, the risk of a contaminated needle subsequently fouling an individual's person is reduced.

Examples of such prior art guard apparatus can be found in U.S. Pat. Nos. 4,731,059, 4,643,199, 4,425,120, 4,770,655, 4,710,170, 4,728,320, 4,702,738, 4,801,295, and 4,634,428. While these prior art devices provide guards for covering or shielding a needle and syringe combination, they are uniformly cumbersome and complex. As such, the devices are not in wide spread use for a variety of reasons.

SUMMARY OF THE INVENTION

It is an object of the present invention to reduce the risk of needle-stick injuries and subsequent disease transmission that may result from these injuries. The present invention, incorporating a guard assembly, is a simple one, two or three piece unit, depending on the embodiment, and can optionally include an easily operated latching mechanism for manipulating the guard between an extended and retracted position. Further, the present invention has a simplified needle disposal technique whereby the needle is positively destroyed and contained within the locked guard and syringe barrel combination.

The present invention includes several embodiments, either with or without a latching mechanism for maintaining the guard in a retracted position. Further, the several embodiments herein disclosed include adapter mechanisms for standard syringe barrels so that the present invention may be used with the present stock of existing syringes.

Additional features and advantages of the present invention will become apparent upon the reading of the following description in association with the drawings and appended claims, which form a part thereof.

BRIEF DESCRIPTION OF THE DRAWINGS

FIG. (1a) is an isometric view of a guard and syringe assembly according to the present invention.

FIG. (1b) is an exploded isometric view of a guard and syringe combination according to the present invention.

FIGS. 2a-d are elevational and sectional views of a guard and syringe assembly according to the present invention of the embodiment shown in FIG. 1.

FIGS. 3a and 3b are exploded front and elevational views of a guard and end-piece combination according to the present invention without an end-latch.

FIGS. 5a and 5b are exploded front and elevational views of a guard according to the present invention including a latching mechanism.

FIG. 5c is an elevational view of a guard assembly according to the present invention including a latching mechanism.

FIGS. 6a-c comprise sectional and elevational views of guard and syringe combination of the embodiment shown in FIG. 5.

FIGS. 7a-d are end and sectional views of a moving plate assembly incorporated in the guard of the present invention of the embodiment shown in FIG. 1.

FIGS. 8a-b are end views of a moving plate assembly according to the present invention of an alternative end piece embodiment for use in the guard embodiment shown in FIG. 1.

FIGS. 9a-c are end and side views of an adapter according to the present invention.

FIGS. 10a-b are side and end views of a combination needle and adapter according to the present invention.

FIGS. 11a-b are end and side views of a syringe barrel according to the present invention.

FIG. 12 is an exploded longitudinal section of the guard assembly of FIG. 1 according to the present invention.

FIGS. 13a-c are perpendicular sectional views of the guard assembly shown in FIG. 12.

FIGS. 14a-b are exploded elevational and front views of a guard and syringe assembly according to the present invention with a hinged cap-piece and sliding impenetrable cup.

FIGS. 15a-b and 16a-c are elevation and sectional views of a guard and syringe assembly according to the present invention of the embodiment shown in FIG. 14.

FIGS. 18a and 18b are elevation and sectional views of a guard and syringe assembly according to the present invention with a fixed impenetrable cup incorporated in the hinged cap-piece.

FIG. 20a is an exploded sectional elevation of a guard assembly according to the present invention.

FIGS. 20b and 20c are sectional views of an alternative caplatch according to the present invention for use on the hinged cap embodiments.

FIGS. 21-f are elevation and sectional views of a syringe guard combination according to the present invention without syringe latch and without cap-piece.

DETAILED DESCRIPTION OF THE PREFERRED EMBODIMENT

Figure 3C:
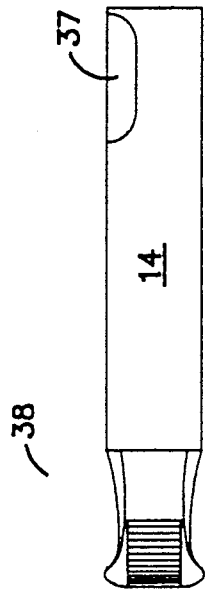
FIG. 3c is an isometric view of a thumb wheel according to the present invention.
Figure 3D:
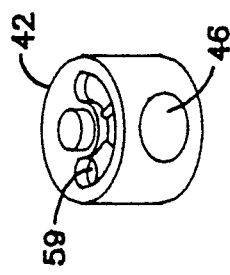
FIG. 3d is an elevational view of a guard and end-piece combination according to the present invention without an endlatch.

A guard and syringe combination is shown in FIGS. 1a and 1b and is generally designated by numeral 10. The guard and syringe combination includes a syringe barrel portion 12, a guard 14, and an end-piece 16. The syringe barrel is of a commercially available variety, and is composed of molded plastic and accommodates a plunger for injecting or withdrawing fluid through the needle 15.

The guard portion 14 forms a cylindrical barrel open at one end and substantially closed at the other. The open end telescopes over the forward end of a syringe barrel so as to enclose the needle attached to the forward end of the syringe barrel. To aid in the alignment and guidance of the syringe barrel within the guard, the guard is equipped with syringe removal slots 35 and interference protrusions 17 (shown in FIG. 12). The syringe removal slots 35 engage and guide tabs 13 on the syringe barrel into latching L-slots 34 (discussed hereinafter), thereby securely engaging the syringe and guard assembly. The interference protrusions 17 engage and slide along the barrel of the syringe so as to aid in aligning the syringe and guard longitudinally. This precise alignment between the guard and syringe barrel assures accurate alignment of needle 15 within the guard 14.

The guard 14 includes an end-piece 16 attached to the substantially closed end of the guard. The end-piece comprises a mechanism for alternately opening a passage aperture, and closing this passage aperture, through which the needle passes for use.

In the embodiment shown in FIG. 1, guard 14 includes an end-piece 16. The end-piece is comprised of a cap-piece 18 and a gripping band 20. Located between the cap-piece 18 and the gripping band 20 is a sliding plate member 22. This cap-piece and plate member may take on several designs as will be discussed later.

The end-piece 16 is rotatably engaged on the end of guard 14 about cylinder 29. Cylinder 29 has an aperture passing through the center thereof (unnumbered), which aperture provides a throughway for the needle to pass from the syringe barrel 12.

Pin 27 extends from a forward end of cylinder 29 and engages slot 26 in sliding plate 22. The relative movement between slot 26 and pin 27 enable sliding plate 22 to move between two positions upon rotation of endpiece 16 with respect to guard 14. Specifically, sliding plate 22 includes aperture 24 as well as impenetrable surface portion 28. By moving the sliding plate so that aperture 24 and impenetrable surface 28 alternately align with aperture 25, a user may either permit or prevent passage of a needle 15 through aperture 25 in cap-piece 18.

In this manner, a user of the guard and syringe combination according to the present invention may selectively encapsulate the needle between uses or permanently encapsulate the needle subsequent to use.

To aid in positively locating the syringe barrel 12 and guard 14 longitudinally with respect to one another, the guard is equipped with latch mechanism 30. The latch in this embodiment is molded integrally with guard 14, having a latching portion and a levering portion. A pivoting linking portion connects the respective latching and levering portions and enables engagement and disengagement of the latch from tab 13. The pivoting linking portion engages a raised portion of the guard by way of latch pins 31. In this manner, pressure exerted on the levering portion results in a pivoting action being imparted to the latching portion so as to raise and lower the latching portion to clear tab 13. (See FIG. 2b explained below.)

The sequence of operation of the guard and syringe combination disclosed in FIG. 1 will be explained with reference to drawing FIGS. 2a-2d.

FIG. 2a shows an elevational view of a guard and syringe assembly according to the present invention. Guard 14 telescopically envelopes the forward end of syringe barrel 12. The guard includes end piece 16 and latch 30. Also shown in this Figure is optional textured surface area 37 which facilitates labeling of the syringe guard combination, by the user, with a variety of writing instruments. This Fig. shows the syringe and guard in the fully extended "as packaged" configuration.

FIG. 2b shows the guard and syringe of FIG. 2a in the "as packaged" configuration, but in a partial sectional view so as to expose the working portions of the guard. The forward end of guard 14 includes latch 30 mounted thereon. The latch includes the respective latching and levering portions as previously discussed. (Note that the syringe barrel and guard are rotated with respect to one another such that FIGS. 2a and 2b demonstrate the latched position.) For the syringe barrel 12 and guard member 14 to be relatively telescopically movable, the barrel and guard must be rotated with respect to one another 90 degrees so that tabs 13 disengage latching L-slots 34 and align with longitudinal slots 32, as shown in FIGS. 2c and 2d.

FIG. 2c shows the guard 14 and syringe 12 in the fully retracted configuration, with the latching portion of latch 30 securely engaged about tab 13. The guard 14 and syringe 12 are securely fixed in this retracted and "ready for use" configuration until an operator releases latch 30 and returns the guard and syringe to the fully extended configuration shown in FIG. 2b. Location of latch 30 on guard 14 allows an operator to release latch 30 prior to withdrawing the needle from the patient. By holding the guard stationary an operator may keep the needle shielded as it is withdrawn from the patient until it is safely contained by guard 14. Subsequent to returning the guard and syringe to this configuration, an operator may optionally latch tabs 13 into latching L-slots 34 so as to secure the guard and syringe in the fully extended configuration. Also, an operator may optionally close aperture 25 by relatively rotating the guard and end-piece 16. In this manner, the needle is completely encapsulated within guard 14.

After an operator has completed the utilization of the needle and syringe, the guard and syringe are placed in the fully extended configuration. The end-piece 16 and guard are rotated so as to close aperture 25 with plate 22, and the guard and syringe are telescoped to the fully retracted configuration by placing the end surface of cap-piece 18 perpendicular to and against a surface applying pressure axially to positively destroy needle 15. This configuration is shown in FIG. 2d. In this manner, the contaminated needle is thereafter unable to foul a person or attendant object.

FIGS. 3a–d show an alternative embodiment of a guard according to the present invention. The alternative embodiment includes a guard portion 14 in combination with a particular end-piece which is cast integrally with the guard. End-piece 38 includes stirrup portions 40. Stirrups 40 extend and surround a thumb wheel 42. Thumb wheel 42 is held in position on stirrups 40 by a clip member 44. The thumb wheel 42 includes an aperture 46 which, by rotation, selectively allows passage of a needle through the end portion of guard 14. The thumb wheel is rotatable between three positions wherein the aperture 46 is aligned with the needle passing through guard 14, in a second position wherein the aperture 46 is releasably held perpendicular to the passage 48 through guard 14, or a third position wherein the aperture 46 is substantially permanently held in a position perpendicular to the passage of a needle 15.

FIG. 3c shows the thumb wheel in isometric view. This view shows the locking mechanism for the thumb wheel. Specifically, thumb wheel 42 includes a locking aperture 59 which engages locking pin 57 on stirrups 40. Hence the thumb wheel may be rotated in two directions. A first direction which allows re-rotation of the thumb wheel back to a position to allow passage of needle 15, and a second direction which positively locks the thumb wheel in a blocking position for permanent disposal of the guard and syringe combination.

In this manner, the rotatable thumb wheel 42 enables a user to selectively encapsulate or allow passage of a needle through guard 14. This sequence of operation is demonstrated in FIGS. 4a–c.

Figure 4C:
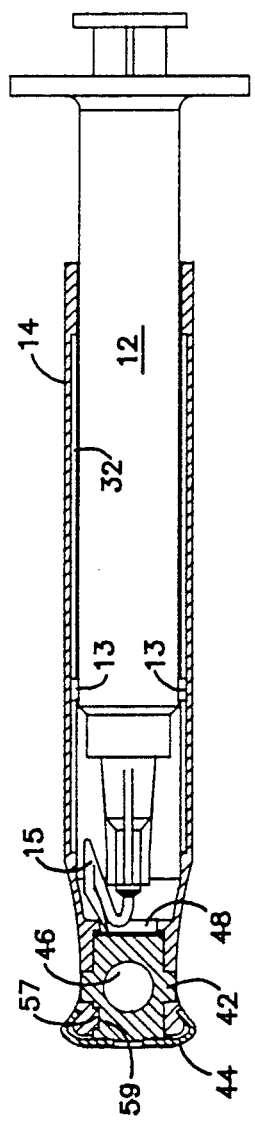
FIG. 4a-c are sectional views of a guard and syringe combination according to the present invention of the embodiment disclosed in FIG. 3.
Figure 4B:
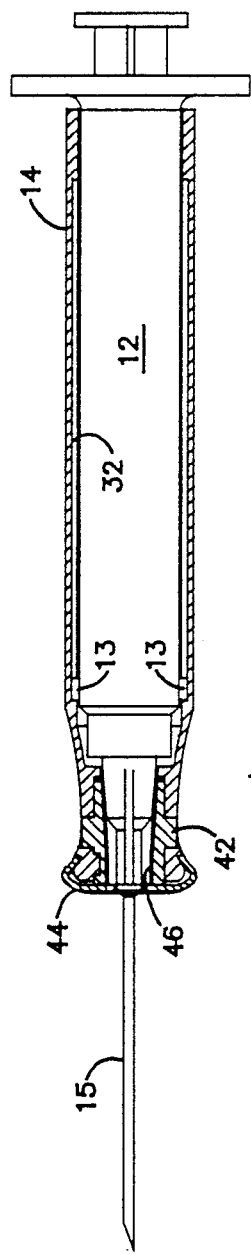
Figure 4A:
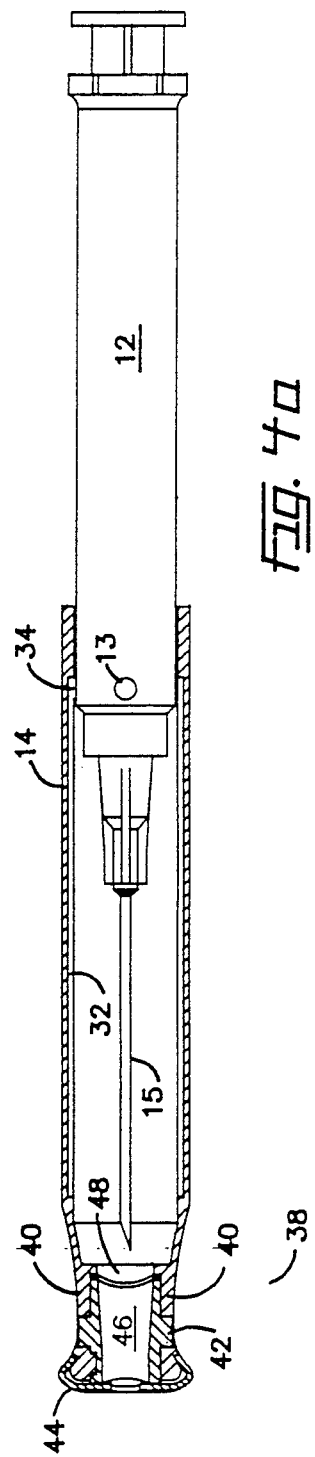

FIG. 4a shows a syringe 12 installed in guard 14 including end-piece 38. FIG. 4a is a sectional view of the guard and a plan view of the syringe barrel and needle combination. In FIG. 4a, thumb wheel 42 is shown with aperture 46 in alignment with needle 15. From this configuration, a user merely rotates guard 14 and barrel 12 to an unlatched position, and moves guard 14 to a retracted position with respect to syringe barrel 12.

FIG. 4b demonstrates the guard 14 and barrel 12 in the fully retracted configuration. In this configuration, the needle 15 is exposed and may be used for either injecting or withdrawing a sample as desired.

FIG. 4c demonstrates the disposed and needle destroyed configuration of the guard and syringe combination. The transition from "in use" in FIG. 4b to disposal in FIG. 4c is as follows. Once a sample has been withdrawn or injected and the syringe is otherwise ready for disposal, the syringe and guard combination are returned to the fully extended configuration as demonstrated in FIG. 4a. By holding the guard stationary an operator may keep the needle shielded as it is withdrawn from the patient until it is safely contained by guard 14, Once in this configuration, thumb wheel 42 is rotated 90 degrees so that aperture 46 is no longer aligned with needle 15 and locking aperture 59 and locking pin 56 engage. The guard and syringe barrel combination is then telescopically moved to the fully retracted configuration by placing clip member 44 perpendicular to and against a surface, applying pressure axially, crushing needle 15 against thumb wheel 42. In this manner, the needle 15 is destroyed and encapsulated so that the possibility of its fouling the user or a subsequent individual which encounters the syringe is significantly reduced.

Also shown in these drawing figures is the interaction of guide slots 32 and guide tabs 13. Guide tabs 13 slide along slots 32 and, in combination with latching L-slots 34 (shown in FIGS. 1 and 12), provide a mechanism for latching the guard and syringe barrel in the extended position shown in FIG. 4a. (Note that the syringe barrel and guard are rotated with respect to one another such that FIG. 4a demonstrates the latched position.) For the syringe barrel 12 and guard member 14 to be relatively telescopically movable, the barrel and guard must be rotated with respect to one another 90 degrees so that tabs 13 disengage latching L-slots 34 and align with longitudinal slots 32, as shown in FIGS. 4b and 4c.

FIG. 5 discloses an alternative embodiment of the thumb wheel embodiment shown in drawing FIG. 3. This embodiment of the invention includes an end-piece 50 which includes stirrups 56, thumb wheel 52 (substantially similar to thumb wheel 42), and latch 54. In this embodiment, latch 54 includes a clip which holds thumb wheel 52 on stirrups 56 and an aperture 61 which engages guide tab 13 when the guard and syringe barrel are in the fully retracted position (Shown in FIGS. 6a–c). Thumb wheel 52 also includes an aperture 58 which permits passage of a needle there through.

Figure 6A:
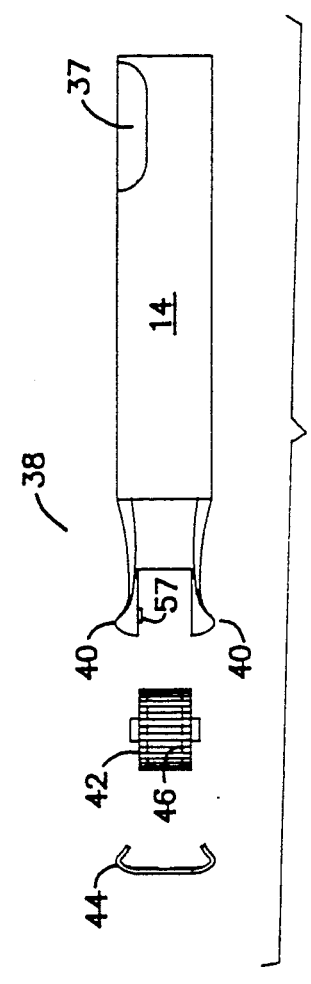
Figure 6B:
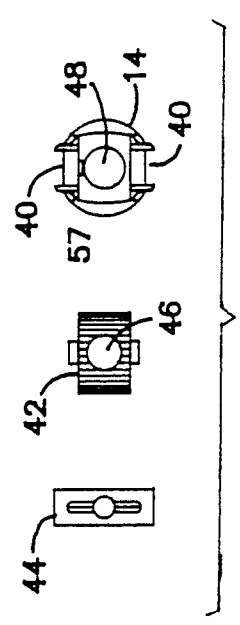

The sequence of operation of the guard and end-piece shown in FIG. 5 is demonstrated in FIGS. 6a–c. FIG. 6a shows a sectional view of guard 14 in combination with a plan view of syringe barrel 12. The syringe barrel fits telescopically within the guard 14 with needle 15 protruding towards the thumb wheel 52. Thumb wheel 52 is shown aligned with needle 15 such that aperture 58 will enable passage of needle 15. The guard 14 and barrel 12 are moved to the fully retracted configuration shown in FIG. 6b and the syringe is ready for use.

FIG. 6b shows the interaction of latch 54 and tab 13. Latch 54 includes a latching aperture 61 on a forward tab portion of the latch. This latching aperture 61 slips over and clips on to tab 13 when the guard 14 and barrel 12 are in the fully retracted configuration. To release the latch, a user exerts force in the direction of the dotted arrow shown in FIG. 6b. Such force will result in a pivoting motion of the forward tab portion of latch 54 so that aperture 61 can clear tab 13 and the telescoping function of the respective guard 14 and barrel 12 is once again achieved.

The sequence of operation whereby needle 15 is destroyed is identical to that disclosed with respect to FIG. 4. Specifically, once a user is finished with the syringe and needle combination, the guard and barrel are returned to the fully extended configuration, thumb wheel 52 is rotated so that aperture 58 no longer aligns with the needle and the thumb wheel is in the locked position, the barrel and guard combination is then returned to the fully retracted configuration by placing clip portion of latch 54 perpendicular to an against a surface, applying pressure axially, crushing needle 15 between thumb wheel 52 and syringe barrel 12.

FIG. 7 discloses an embodiment of the sliding plate 22 embodiment of the present invention. Cap-piece 18 includes sliding plate 22. Plate 22 includes slot 26 which engages and interacts with actuating pin 27. Plate 22 further includes aperture 24 and impenetrable surface 28. Upon relative rotation of the guard and end-piece, pin 27 translates plate 22 to a position so as to align either aperture 24 or impenetrable surface 28 with aperture 25. In this way, aperture 25 is selectively blocked left open so as to allow needle 15 to pass there through. When a user has determined that the syringe and needle combination should be destroyed, end piece 16 is rotated past the point necessary to position plate 22 over aperture 25. In this manner, pin 27 is sheared and no longer able to impart movement to plate 22. Hence, plate 22 is positioned so as to permanently block aperture 25. The guard and syringe barrel are then moved to the respectively retracted configuration so as to destroy and disable the syringe and needle combination.

FIG. 8 discloses an alternative embodiment of the sliding plate 22 embodiment of the present invention which may be incorporated in the end-piece of guard 14 shown in FIG. 1. Cap-piece 36 includes sliding plate 23 which selectively leaves open or blocks aperture 25 in the forward end of guard 14. Pin 27, mounted on cylinder 29, engages plate 23 and rotates and slides the plate upon relative rotation of the end-piece and guard 14 so that the plate moves from the position shown i FIG. 8a to that shown in FIG. 8b. When the user has determined that the needle and syringe should be destroyed/disabled, the user twists the end cap and barrel to the extent necessary to position plate 23 over aperture 25. The open aperture 25 in the cap is irreversibly closed by this action. Subsequent to placing plate 23 in this position, the guard and barrel are moved telescopically to the fully retracted position crushing needle 15.

The above described sliding plate and end cap apparatus may be comprised of plastic or other suitable material which resists penetration of the variety of needles presently in use for medical or other purposes.

FIG. 9 shows an adapter for use with existing syringe barrel stock so as to adapt an existing syringe barrel for use with a guard according to the present invention. The adapter fits between an existing syringe and needle attachment so that a guard according to the present invention can be used there with. The particular features of the adapter which enable such usage are the inclusion of guide tabs 13 for engagement in slots 32 of guard 14.

FIG. 10 shows a needle adapter combination. Needle adapter combination 72 is equipped with guide tabs 13 which also engage slots 32 and enable the use of a guard according to the present invention in combination with a standard syringe barrel.

FIG. 11 discloses a syringe barrel for use with the present invention. The particular feature of the barrel which enables use with a guard according to the present invention is the inclusion of guide tabs 13.

FIG. 12 is an exploded longitudinal section of guard 14 of the embodiment shown in FIG. 1. This Fig. shows the pivoting and connecting relationship between the respective end piece members and the location of interference protrusions 17. This Fig. also shows syringe removal slots 35, latching L-slots 34, guide slots 32 and their constricted latching ends and junctions which give an operator precise control locating guard 14 with respect to syringe barrel 12.

FIG. 13 shows sectional views of the guard embodiment shown in FIG. 12 along the indicated sections, including end view FIG. 13c. FIG. 13a shows the particular location of locking slots 34 and their relationship to guide slots 32. FIG. 13b shows the location of syringe removal slots 35. FIG. 13c shows an end view of the guard 14, and discloses the location of interference protrusions 17.

FIGS. 14a shows an alternative embodiment of a guard syringe assembly according to the present invention. This Fig. is an exploded elevational view. The alternative embodiment includes a guard portion 14 in combination with a particular end-piece 73 which incorporates a hinged cap-piece. End-piece 73 includes cap-piece 18 connected to gripping band 20 by hinge 80. Hinge 80 has two stable positions, the cap-piece open position as disclosed in this figure and the cap-piece closed position as disclosed in FIG. 15. Cap-piece 18 further comprises impenetrable cover 76, cap latch 74, locking grooves 78 and needle capture material 87. Cap latch 74 engages latching rib 75 on gripping band 20 when the cap is in the closed position. Impenetrable cover 76 further comprises locking edges 77 which engage locking grooves 78 when the syringe guard assembly is operated in the needle destruction mode.

FIG. 14b shows a front elevational view of cap-piece 18 hinged to gripping band 20 by hinge 80. Also shown are cap latch 74, latching rib 75 and needle capture material 87.

FIG. 15a shows an elevational view of the guard and syringe assembly of FIG. 14a. Guard 14 telescopically envelopes the forward end of syringe barrel 12. The guard includes end-piece 73 and latch 30. This Fig. shows the guard and syringe assembly in the fully extended "as packaged" configuration.

FIG. 15b shows the guard and syringe assembly of FIG. 15a in the fully extended "as packaged" configuration, but in a partial sectional view so as to expose the working portions of the guard. The forward end of guard 14 includes integrally molded latch 30. The latch includes the respective latching and levering portions as previously discussed and further disclosed in FIG. 20. (Note that the syringe barrel and guard are rotated with respect to one another such that FIGS. 15a and 15b demonstrate the latched position.) For the syringe barrel 12 and guard member 14 to be relatively telescopically movable, the barrel and guard must be rotated with respect to one another 90 degrees so that tabs 13 disengage latching L-slots 34 and align with longitudinal slots 32, as shown in FIGS. 16a-c.

FIG. 16a shows the guard and syringe assembly of FIG. 15b with cap-piece 18 in the open position, guard 14 in the fully retracted position, and the latching portion of latch 30 securely engaged about tab 13. With the syringe guard assembly in this configuration an operator may rotate gripping band 20, which is rotatably engaged on cylinder 29, to position cap-piece 18 so that it will not interfere with proper needle bevel orientation during an injection. The guard 14 and syringe 12 are securely fixed in this retracted and "ready for use" configuration until an operator releases latch 30 and returns the guard to the fully extended position. Location of latch 30 on guard 14 allows an operator to release latch 30 prior to withdrawing the needle from the patient. By holding the guard stationary an operator may keep the needle shielded as it is withdrawn from the patient until it is safely contained by guard 14.

At this time an operator may optionally latch tabs 13 into latching L-slots 34 so as to secure the guard and syringe in the fully extended configuration. Also an operator may optionally close cap-piece 18 engaging cap latch 74 with latching rib 75 on gripping band 20. In this manner, needle 15 is completely encapsulated within guard 14.

FIG. 16b shows the guard syringe assembly of FIG., 16a. This figure is a partial sectional view showing the guard and syringe assembly in the fully retracted configuration ready for disposal. After an operator has completed the utilization of the needle and syringe, an injection for example, the guard and syringe are placed in the fully extended configuration. As previously discussed, this may be accomplished as the needle is withdrawn from a patient. Cap-piece 18 is pivoted on hinge 80 to the closed position engaging cap latch 74 with latching rib 75. The guard and syringe are telescoped to the fully retracted configuration by placing impenetrable cover 76 perpendicular to and against a surface applying pressure axially. As the guard is forced to the fully retracted position, impenetrable cover 76 will slide over cap-piece 18 until locking edges 77 engage locking grooves 78 and at the same time cover 76 will engage cap latch 74 disabling the latch in the locked position as shown in this figure. Also shown is needle 15, destroyed as a result of forcing the guard to the fully retracted position. Needle 15 has penetrated needle capture material 87 of cap-piece 18 and has been stopped by impenetrable cover 76 causing it to collapse. In this manner, the contaminated needle has been encapsulated and destroyed.

FIG. 16c shows an elevation of the guard and syringe 15 assembly of FIG. 16b. The needle has been encapsulated and destroyed. Cap-piece 18 has been substantially permanently locked in the closed position. The syringe guard assembly is now ready for safe disposal.

Figure 17B:
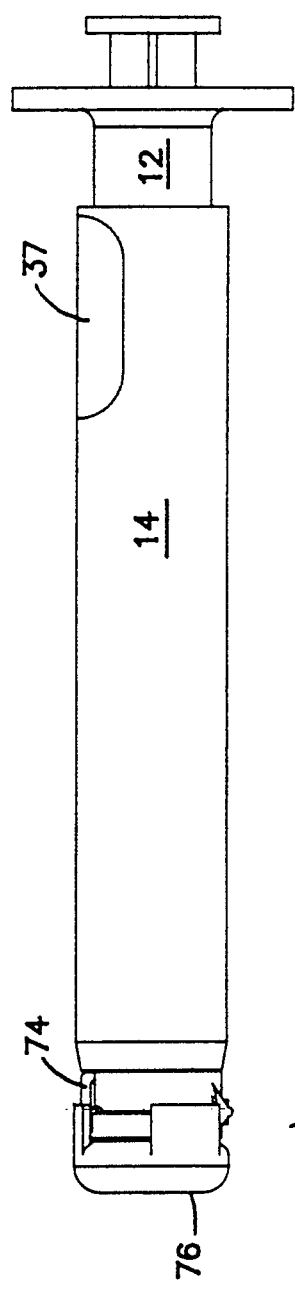
FIGS. 17a and 17b are elevation and sectional views of a guard and syringe assembly according to the present invention without an end-piece syringe latch.
Figure 17A:
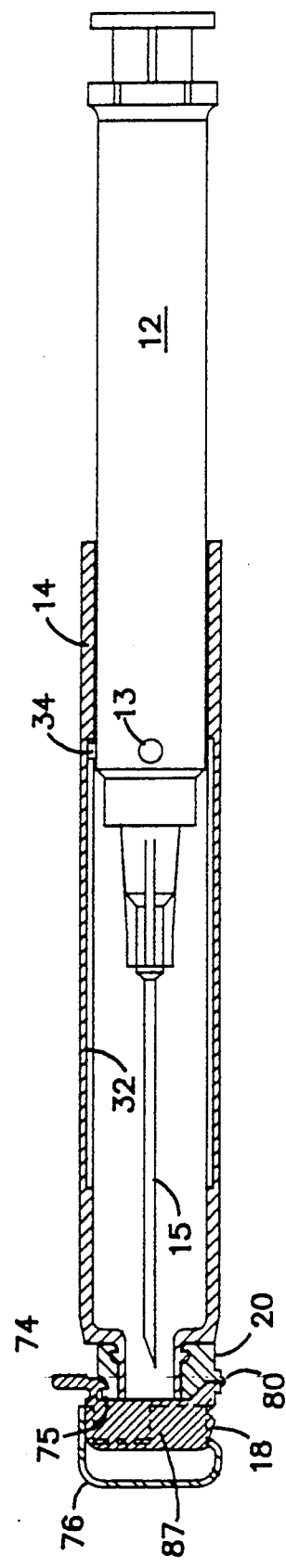

FIG. 17a discloses an alternative embodiment of the hinged cap embodiment of FIG. 16. A partial sectional view of a guard and syringe assembly is shown. Guard 14 telescopically envelopes the forward end of syringe barrel 12. The guard includes end-piece 73 without syringe latch 30. This Fig. shows the syringe and guard in the fully extended "as packaged" configuration.

FIG. 17b shows an elevation of the guard and syringe assembly of FIG. 17a. The needle has been encapsulated and destroyed. Cap-piece 18 has been substantially permanently locked in the closed position. The syringe guard assembly is ready for safe disposal.

FIG. 18a discloses an alternative embodiment of the hinged cap embodiment of FIG. 16. A partial sectional view of a guard and syringe assembly is shown. Guard 14 telescopically envelopes the forward end of syringe barrel 12. The guard includes end-piece 73 with latch 30 and impenetrable cup 82 incorporated in cap-piece 18. This Fig. shows the syringe and guard in the fully extended "as packaged" configuration.

FIG. 18b shows an elevation of the syringe and guard assembly of FIG. 18a. The needle has been encapsulated and destroyed. The syringe guard assembly is now ready for safe disposal.

Figure 19B:
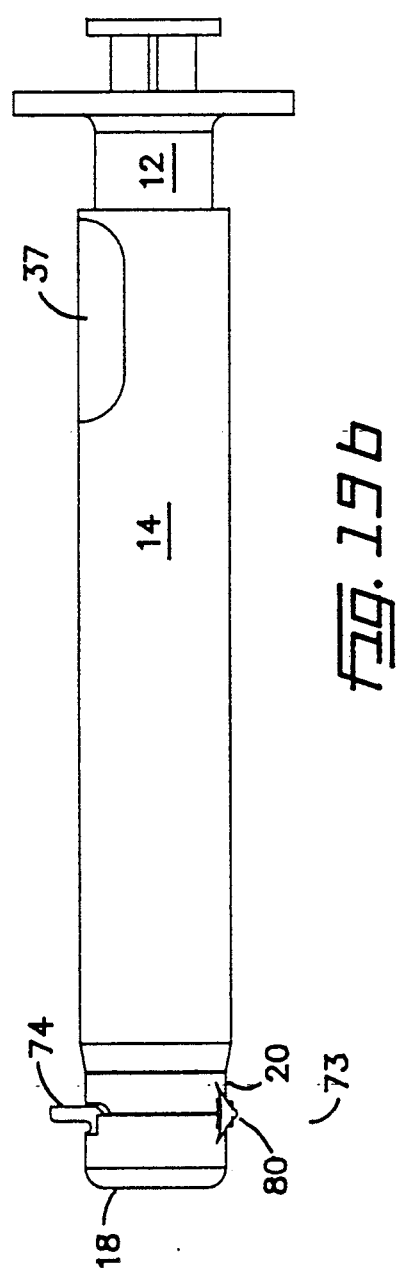
FIGS. 19a and 19b are elevation and sectional views of a guard and syringe assembly according to the present invention without an end-piece syringe latch and with a fixed impenetrable cup incorporated in the hinged cap-piece.
Figure 19A:
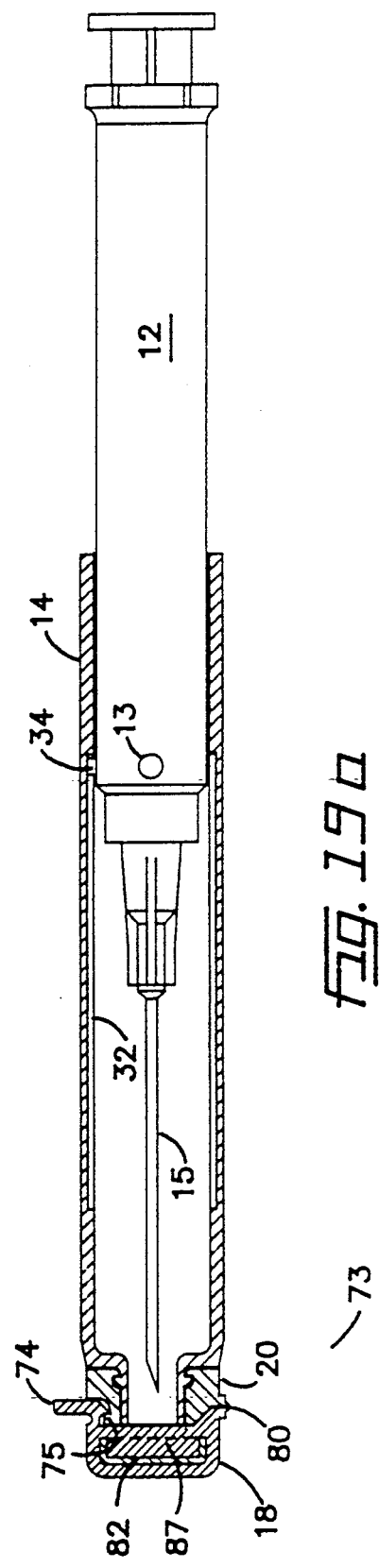

FIG. 19a discloses an alternative embodiment of the hinged cap embodiment of FIG. 17. A partial sectional view of a guard and syringe assembly is shown. Guard 14 telescopically envelopes the forward end of syringe barrel 12. The guard includes end-piece 73 without syringe latch 30. Impenetrable cup 82 is incorporated into cap-piece 18. Aside from the inclusion of an impenetrable member in or surrounding hingeable cap 18, the cap 18 may be constituted of a material which is itself impenetrable to a degree sufficient to destroy needle 15. FIG. 19a shows the syringe and guard in the fully extended "as packaged" configuration.

FIG. 19b shows an elevational view of the syringe and guard assembly of FIG. 19a. The needle has been encapsulated and destroyed. The syringe guard assembly is now ready for safe disposal.

FIG. 20a shows an exploded sectional elevational view of the guard of the embodiment shown in FIGS. 14, 15, and 16. This Fig. shows the pivoting and connecting relationship between the respective end piece members. This figure also shows syringe removal slots 35, interference protrusions 17, and syringe latch pins 31.

FIGS. 20b and 20c disclose an alternative embodiment of cap latch 74 of the hinged cap embodiments of the present invention. In this embodiment cap latch 74 includes break-away portion 91, slits 92 and edge 93. After an operator has completed the utilization of the syringe guard combination, placed it in the fully extended configuration and closed cap-piece 18, break-away portion 91 may be removed disabling cap latch 74 in the closed position. Break-away portion 91 is removed by levering it on edge 93 of latch 74 to spread slits 92 until latch 74 is fractured and break-away portion 91 separated as shown in FIG. 20c. In this manner, cap-piece 18 is substantially permanently locked in the closed position.

FIG. 21a discloses an alternative embodiment of a syringe guard combination according to the present invention. This embodiment is directed toward syringes used for self administered injections. The alternative embodiment includes a particular guard portion 84 in combination with a particular end-piece 83 which is cast integrally with the guard. End-piece 83 incorporates syringe position tabs 85, syringe locking wedges 86 and needle capture material 87. This Fig. is an exploded partial sectional view and also shows syringe barrel 12, needle 15, and locking groove 90.

FIG. 21b is a sectional view of guard 84 of FIG. 21a showing syringe locking wedges 86.

FIG. 21c shows an elevational view of the syringe guard combination of FIG. 21a. Guard 84 telescopically envelopes the forward end of syringe barrel 12. This figure shows the syringe and guard in the fully extended "as packaged" configuration.

FIG. 21d is a partial sectional elevation of syringe guard combination of FIG. 21c. This view shows the syringe guard combination in the fully extended "as packaged" configuration. Syringe position tabs 85 locate syringe barrel 12 until guard 84 is removed.

FIG. 21e is a partial sectional elevation of the syringe guard combination of FIG. 21d. This view shows the syringe guard combination in the fully retracted position ready for disposal. Following use, syringe 12 is reinserted into guard 84. Prior to disposal, the guard and syringe are telescoped to the fully retracted position by placing the closed end of guard 84 perpendicular to and against a surface applying pressure axially. As the guard is forced to the fully retracted position, needle 12 will partially penetrate capture material 87 of end-piece 83 before collapsing. Locking wedges 86 will engage locking groove 90, locking the syringe into guard 84. In this manner the contaminated needle has been encapsulated and destroyed, allowing for safe disposal of the syringe guard combination.

FIG. 21f discloses an alternative embodiment of the syringe guard combination of FIG. 21e. This Fig. is a partial sectional elevation disclosing impenetrable plate 88 incorporated in guard 84.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

I claim:

1. An assembly adapted for injecting or drawing fluid into or from a surface, said assembly comprising:
    a barrel portion for containing fluid, said barrel being equipped with a needle on an end thereof, said needle being adapted to pass fluid contained in said barrel into or from said substrate;
    tubular guard means telescopically related to and surrounding the end of said barrel equipped with said needle, said guard means having first and second ends and being adapted to telescope along said barrel between a first extended position, and a second retracted position; and
    end-piece means mounted on a first end of said guard means, said end-piece capable of being configured in first and second positions, said first position allowing passage of said needle through said first end of said guard when said guard is moved to said retracted position, said second position of said end-piece means blocking passage of said needle through said first end of said guard means, and enabling positive destruction of said needle when said guard is moved to said retracted position, wherein
    said end piece comprises a cap member which is hingedly attached adjacent to said first end of said guard means and hinges about an axis transverse to the direction of said needle, whereby said cap member can pivot between a position which blocks said needle from passing through said first end of said guard and a second position in which the cap member does not block passage of said needle.

2. An assembly as in claim 1, wherein said end piece further comprises;
    locking means for locking said hingeable cap portion in said second position.

3. An assembly as in claim 1, further comprising:
    latching means for selectively locking said guard and said barrel portion in either of said first extended or second retracted positions.

4. An assembly adapted for injecting or drawing fluid into or from a surface, said assembly comprising:
    a barrel portion for containing fluid, said barrel being equipped with a needle on an end thereof, said needle being adapted to pass fluid contained in said barrel into or from said substrate;
    tubular guard means telescopically related to and surrounding the end of said barrel equipped with said needle, said guard means having first and second ends and being adapted to telescope along said barrel between a first extended position, and a second retracted position; and,
    cap means for closing off sand first end of said guard means, said cap means being pivotally mounted on said first end of said guard means so as to pivot about an axis transverse to the direction of said needle between first and second positions, said first position allowing passage of said needle through said first end of said guard when said guard is moved to said retracted position, said second position of said cap means blocking passage of said needle through said first end of said guard means, and enabling positive destruction of said needle when said guard is moved to said retracted position.

5. An assembly as in claim 4, wherein said cap means further comprises:
    locking means for locking said hingeable cap portion in said second position.

6. An assembly as in claim 5, further comprising:
    latching means for selectively locking said guard and said barrel portion in either of said first extended or second retracted positions.

* * * * *